| United States Patent [19] | [11] | Patent Number: | 4,559,333 |
|---|---|---|---|
| Girijavallabhan et al. | [45] | Date of Patent: | Dec. 17, 1985 |

[54] HYDRAZONE SUBSTITUTED PENEMS

[75] Inventors: Viyyoor M. Girijavallabhan, Parsippany; Ashit K. Ganguly, Upper Montclair; Richard W. Versace, Ringwood; Naginbhai M. Patel, Kearny, all of N.J.

[73] Assignee: Schering Corporation, Kenilworth, N.J.

[21] Appl. No.: 585,314

[22] Filed: Mar. 1, 1984

[51] Int. Cl.$^4$ ................. C07D 499/00; A61K 31/425
[52] U.S. Cl. ............................. 514/192; 260/245.2 R
[58] Field of Search ................. 260/245.2 R, 245.2 T; 424/270, 271; 514/192

[56] References Cited

U.S. PATENT DOCUMENTS

| 4,260,618 | 4/1981 | Christensen et al. ............... 424/263 |
| 4,423,055 | 12/1983 | McCombie .......................... 424/270 |
| 4,443,373 | 4/1984 | Girijavallabhan et al. .... 260/245.2 R |
| 4,448,782 | 5/1984 | Afonso et al. ............... 260/245.2 R |
| 4,482,565 | 11/1984 | Foglio et al. ................ 260/245.2 R |
| 4,485,110 | 11/1984 | Osborne ....................... 260/245.2 R |
| 4,503,064 | 3/1985 | Girijavallabhan et al. ......... 514/210 |

*Primary Examiner*—Nicholas S. Rizzo
*Attorney, Agent, or Firm*—Gerald S. Rosen; Thomas D. Hoffman; Stephen I. Miller

[57] ABSTRACT

There is disclosed 2-(hydrazonoalkylthio)penems and their pharmaceutically acceptable salts and esters and their use as antibacterials.

10 Claims, No Drawings

HYDRAZONE SUBSTITUTED PENEMS

BACKGROUND OF THE INVENTION

This invention relates to 2-(hydrazonoalkylthio)-penems and their pharmaceutically acceptable salts and esters, which compounds possess potent antibacterial activity.

There is a continuing need for new antibacterial agents because continued extensive use of effective antibacterials gives rise to resistant strains of pathogens.

SUMMARY OF THE INVENTION

The novel penem compounds of this invention are represented by the formula

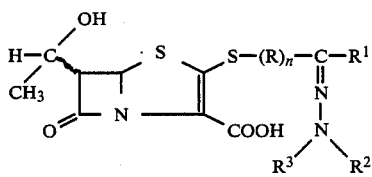

and pharmaceutically acceptable salts and pharmaceutically acceptable esters thereof, in racemic or optically active forms wherein n is one or two;
R represents

wherein $R^4$ and $R^5$ are independently selected from hydrogen, lower alkyl, hydroxy-lower alkyl, halo-lower alkyl, amino-lower alkyl, carbamido-lower alkyl, cyano-lower alkyl, carbamoyloxy-lower alkyl, carbamoyl-lower alkyl, carboxy-lower alkyl, heterocyclyl-lower alkyl wherein the heterocyclic moiety has 5 or 6 ring atoms, at least one of which is carbon, and the remaining 4 or 5 ring atoms are independently selected from carbon, nitrogen, oxygen and sulfur; or $R^4$ and $R^5$ taken together are =O;

$R^1$ represents hydrogen, lower alkyl, hydroxy-lower alkyl, amino-lower alkyl, carboxy-lower alkyl, carbamoyloxy-lower alkyl, carbamoyl-lower alkyl, halo-loweralkyl, cyano-lower alkyl, heterocyclic or heterocyclyl-lower alkyl wherein the heterocyclic moiety has 5 to 6 ring atoms, at least one of which is carbon, and the remaining ring atoms are independently selected from oxygen, carbon, nitrogen and sulfur;

$R^2$ and $R^3$ independently represent hydrogen, carbamoyl lower alkyl, carboxy-loweralkyl, hydroxy-lower alkyl, amino-lower alkyl, imidazolyl-lower alkyl, triazolyl-lower alkyl, tetrazolyl-lower alkyl, pyridinium-lower alkyl, aryl, or $R^2$ and $R^3$ together with the N to which they are attached are a heterocyclic of 5 or 6 ring atoms, at least one of which is carbon and the remaining ring atoms are independently selected from nitrogen and carbon wherein said heterocyclic moiety is unsubstituted or substituted with lower alkyl, hydroxy-lower alkyl, amino-lower alkyl, carboxy-lower alkyl, carboxyl, amino, hydroxy, imidazole-lower alkyl, triazole-lower alkyl, tetrazole-lower alkyl or pyridinium-lower alkyl.

As used herein, the term "lower alkyl" means straight or branched chain alkyl groups of 1 to 6 carbon atoms, e.g. methyl, ethyl, propyl, iso-propyl, butyl, t-butyl, pentyl, neopentyl, hexyl and the like; "halo" means fluorine, chlorine, bromine or iodine, with fluorine preferred; "heterocyclyl" unless otherwise stated means an aliphatic or aromatic heterocyclic group with 5 or 6 ring atoms, at least one of which is carbon, and the remaining 4 or 5 ring atoms are independently selected from carbon, nitrogen and sulfur, the preferred heterocyclics contain a nitrogen bonded to the lower alkyl moiety.

Heterocyclic groups within the scope of this invention are, for example, pyrrole, imidazole, piperidine, pyrrolidine, imidazolidine, pyrazole, triazole, isothiazole, pyridinium, tetrazole, thiadiazole, thiazole, and the like. All position isomers of the heterocyclics are contemplated for examples, 1,2,4-triazole, 4,1,2-triazole, 1,2,3-triazole, 2,1,3-triazole, 1,3-thiazole, 1,2,3,4-tetrazole, 2,1,3,4-tetrazole and the like.

Preferred heterocyclics are imidazole, 1,2,4-triazole, 1,2,3-triazole, 1,3-thiazole and imidazolidine.

"Aryl" as used herein means a phenyl or benzyl either substituted or unsubstituted wherein said substituents are selected from hydrogen, lower alkyl, hydroxy-lower alkyl, carboxy-lower alkyl, carboxyl or amino.

Preferred compounds of formula I are those in which $R^1$ is hydrogen or lower alkyl; and $R^2$ and $R^3$ are each independently hydrogen or carbamoyl or taken together are a nitrogen and carbon containing heterocyclic ring.

The most preferred compounds are those in which n is one; $R^2$ and $R^3$ taken together are a triazole, or $R^2$ is hydrogen and $R^3$ is carbamoyl; and $R^1$ is lower alkyl, and $R^4$ and $R^5$ are each hydrogen.

"Pharmaceutically acceptable salts" as used herein means alkali metal salts such as sodium and potassium salts; alkaline earth metal salts such as calcium, magnesium and aluminum salts; amine salts formed from a wide variety of suitable organic amines, i.e., araliphatic, cycloaliphatic, (cyloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine. Acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic acid and malic acids. The compounds of this invention which contain a 3-carboxylic group and a basic group (the heterocyclic group) form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. Salts can be formed, for example, by treating with metal compounds such as alkali metal salts of suitable carboxylic acids, or with ammonia or a suitable organic amine, wherein preferably stoichiometric amounts or only a small excess of the salt-forming agent is used. Acid addition salts are obtained in the usual manner, for example, by treating with an acid or a suitable anion exchange reagent. Inner salts of the compounds of formula I, i.e., a zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

Compounds of this invention possess 3 or more asymmetric carbon atoms indicated in the partial formula I(a) below at the 5, 6 and 8 and the 2' and 3'-position carbon atoms

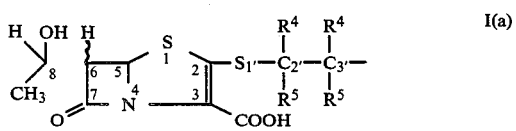

At the 5,6 and 8 positions, compounds of the invention may possess 5R, 6S, 8R or 5R, 6R, 8S stereochemistry at those chiral atoms. The preferred absolute stereochemistry for the compounds of the present invention at those positions is 5R, 6S, 8R.

Compounds of this invention wherein $R^4$ and $R^5$ on the carbon atom are different will have additional asymmetric carbon atom(s) as shown in formula I(a) at the 2' and 3' positions. All the possible resulting stereoisomers are included herein.

DETAILED DESCRIPTION

When tested in standardized microbiological assays, the compounds of this invention are active against such gram-positive organisms as *Staphylococcus aureus* and *Bacillus subtilis,* and such gram-negative organisms as *E. coli* and *Salmonella* at test levels of 0.03 to 2.0 micrograms/ml. Additionally, they show activity against organisms which produce beta-lactamases, e.g., penicillinase and cephalosporinase, indicating a resistance against these enzymes.

The compounds of this invention exhibit low protein binding and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals including humans, having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene glycol polymers; betacyclodextrin; fatty alcohols, hydrolyzed cereal solids; water; polyalkylene glycols; gums; and petrolatum; as well as other non-toxic compatible fillers, binders, disintegrants and lubricants commonly used in pharmaceutical formulations. The compositions may also contain perservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, i.e., the age and weight of the individual being treated, the mode of administration, the potency of the administered compound and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

The compounds of this invention are prepared by the processes disclosed in applicants' assignees' copending U.S. patent application Ser. No. 549,535 entitled "Process for the Production of Penems" filed Nov. 7, 1983. The processes disclosed therein are preferred over other known suitable processes for preparing penems.

The process designated as process A in the aforesaid patent application comprises.

(a) reaction of an azetidinone of the formula

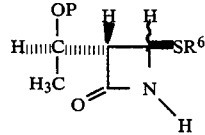

wherein P is a removable hydroxy protecting group or hydrogen; and $R^6$ is a sulfur protecting group selected from triphenylmethyl, diphenylemthyl, 2-pyranyl, or lower alkyl carbonyl; with a compound of the formula IIIa and IIIb $$H_2O + O=C\begin{matrix} M \\ M_1 \end{matrix} \qquad \text{IIIa}$$

$$HO\diagdown_{\phantom{C}}\diagup M \atop HO\diagup^{\phantom{C}}\diagdown M_1 \qquad \text{IIIb}$$

wherein M and $M_1$ are independently —COOCH$_2$CH$_2$R$^7$ or —COOCH$_2$CH=CH$_2$; R$^7$ is trimethylsilyl, t-butyldiphenylsilyl or other equivalently functioning lower alkylsilyl group, cyano or a sulfone of the formula —SO$_2$-aryl; to form the intermediate of the formula IV (Structure IV: OP, H, SR$^6$, H$_3$C, N, OH, C—M, M$_1$)

wherein P, R$^6$, M and $M_1$ are as hereinabove defined;

(b) treatment of the compound of formula IV with a chlorinating agent to form the following compound of formula V (Structure V: OP, H, SR$^6$, H$_3$C, N, Cl, C—M, M$_1$)

wherein P, R$^6$, M and $M_1$ are as defined hereinabove;

(c) treatment of the compound of formula V with a stoichiometric excess of elemental zinc in a strong acid such as hydrochloric acid to effect removal of the chlorine and the removable sulfur and hydroxy protecting groups, and, if a removable hydroxy protecting group is utilized which is not removable with zinc, subsequent removal of said hydroxy protecting group, producing a compound of formula VI (Structure VI: OH, H, SH, H$_3$C, N, H, C—M, M$_1$)

wherein M and $M_1$ are as hereinabove defined;

(d) treatment of the compound of formula VI with a hydroxy protecting group to form the compound of formula VI(a)

(Structure VI(a): OP, H, SH, H$_3$C, N, H, C—M, M$_1$)

wherein M and $M_1$ are defined hereinabove and P is a hydroxy protecting group as defined hereinabove;

(e) reaction of the compound of formula VI or VI(a) with a thiocarbonyl compound of formula VII $$S=C(-Y)_2 \qquad \text{VII}$$

wherein Y is a leaving group; to form a compound of formula VIII (Structure VIII: OP, H, S, S, H$_3$C, N, M, M$_1$)

wherein P, M and $M_1$ are as hereinbelow defined;

(f) treatment of the compound of formula VIII wherein P is a hydroxy protecting group with an aqueous acid solution to deprotect the hydroxy group to form a compound of formula VIII(a)

(Structure VIII(a): OH, H, S, S, H$_3$C, N, M, M$_1$)

wherein M and $M_1$ are as hereinabove defined.

In an alternative procedure, compounds of formula VIII(a) can be prepared from compounds of formula V by eliminating steps (d) and (f) (i.e., the protection and subsequent deprotection of the hydroxyl group at the C-8 position).

(g) treatment of the compound of formula VIII(a) with a fluoride ion (when M is —COOCH$_2$CH$_2$R$^7$ and R$^7$ is trimethyl silyl only one equivalent of fluoride need be used) to form the compound of formula IX(a) which is tautomeric with formula IX(b)

(Structures IX(a) and IX(b) shown in equilibrium)

wherein M is as defined above.

(h) reaction of the tautomer of formulas IX(a) and IX(b) with a compound of formula XII

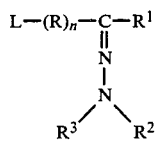

XII wherein L is a leaving group such as trifluoromethan-sulfonyl (triflate), bromine or chlorine, n, R,$R^1$,$R^2$ and $R^3$ are as hereinabove defined, to form a compound of formula XIII

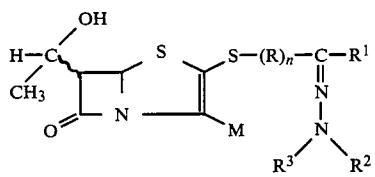

XIII wherein n, R, $R^1$, $R^2$, $R^3$ and M are as hereinabove defined.

(i) treatment of a compound of formula XIII under catalytic conditions when M is —COOCH$_2$CH=CH$_2$ to remove the allyl protecting group in the presence of an alkali base (if the product is a zwitterion, deprotection requires only the catalyst and any mild nucleophile, e.g., H$_2$O, alcohol, etc.) or if M is —COOCH$_2$CH$_2$$R^7$, treating the compound of formula XIII with one equivalent of fluoride ion to form the compounds of formula I.

The preferred process for producing the compounds of this invention is referred to as Process C in the aforementioned patent application and comprises the steps of (a) reaction of the azetidinone of formula II in which P is hydrogen as in the following formula II(a)

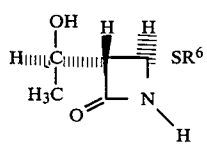

II(a)

wherein $R^6$ is a sulfur protecting group selected from triphenylmethyl, diphenylmethyl, 2-pyranyl, or lower alkyl carbonyl; with an alpha-substituted allyl acetate of formula XIV

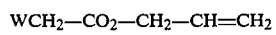

XIV wherein W is a leaving group; to form the intermediate of the formula

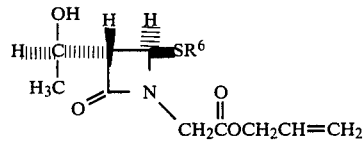

XV wherein $R^6$ is as defined hereinabove.

(b) treatment of the compound of formula XV with a stoichiometric excess of elemental zinc in a strong acid to deprotect the sulfur and form the compound of formula XVI

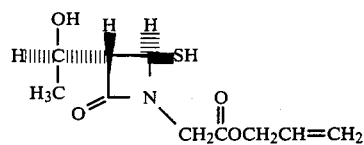

XVI (c) treatment of the compound of formula XVI with a hydroxy protecting group to form the compound of formula XVI(a)

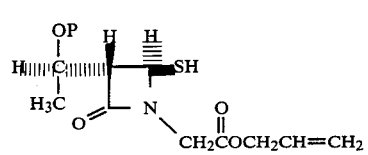

XVI(a)

wherein P is a hydroxy protecting group as hereinabove defined;

(d) reaction of the compound of formula XVI or XVI(a) with a thiocarbonyl compound of formula VII

S=C(—Y)$_2$   VII wherein Y is a leaving group to form a compound of formula XVII

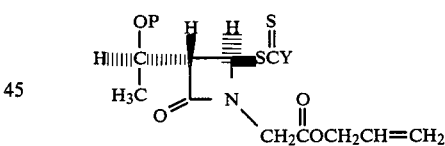

XVII wherein Y and P are as hereinabove defined;

(e) treatment of compound XVII with a nonnucleophilic strong base to form a compound of formula IX(a') which is tautomeric with formula IX(b')

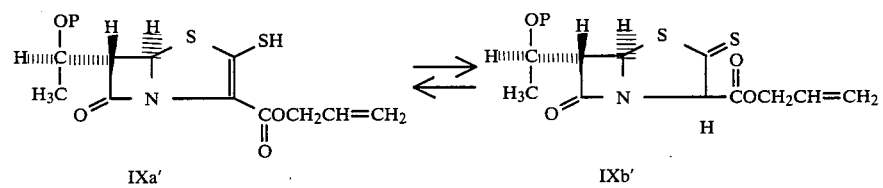

wherein P is as hereinabove defined;

(f) treatment of the tautomer of formulas IX(a') and IX(b') under conditions which effect removal of the hydroxy protecting group when P is a hydroxy protecting group.

Following steps (h) and (i) of Process A as applied to the tautomer of formulas IX(a') and IX(b') yields compounds of formula I.

In the most preferred embodiment, the substituted allyl acetate of formula XIV is added to the azetidinone of formula II(a) to form the intermediate of formula XV. The intermediate of formula XV is then utilized directly in steps (b), (c) and (d) which are conducted sequentially without isolation of any intermediates.

Likewise steps (e) and (f) are preferably conducted sequentially without the necessity of isolating any intermeidates.

Step (a) involves the reaction of an azetidinone of formula II(a) at 15°–30° C. in the presence of an acid acceptor with an alpha-substituted allyl acetate of formula XIV to form the compound of formula XV. Preferred W leaving groups in the compound of formula XIV include tosyl, mesyl, chloro, bromo, iodo, and trifluoromethanesulfonyl. Particularly preferred W leaving groups are iodo and bromo.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) involves the conversion of the compound of formula XV to the corresponding thiol of formula XVI by deprotecting the sulfur with a stoichiometric amount of elemental zinc in hydrochloric acid. Step (c) involves the protection of the 6-hydroxy substituent to form the compound of formula XVI(a) with the preferred protecting group being trimethylsilyl, whereas step (d) is that wherein a compound of formula XVI or XVI(a) is converted to a compound of formula XVII by addition of a thiocarbonyl reagent of formula VII wherein the Y leaving group is typically imidazolyl, chloro, bromo, or iodo.

In Step (b) typically, a polar solvent such as methylene chloride, methanol, ethanol, dimethylformamide (DMF), tetrahydrofuran, dimethylsulfoxide or acetonitrile is utilized. Water, or any proton source, adjusted by the addition of a strong acid, is added to enhance the activity of zinc. Typical temperatures range from −15° C. to about room temperatures (about 25° C.) with a temperature of about 0° C. being preferred. The removable hydroxy and sulfur protecting groups used are preferably those which are removable by elemental zinc. In the event a removable hydroxy protecting group is used which is not removable by zinc, a separate removal step is conducted to remove the hydroxy protecting group by means well known in the beta-lactam art. This separate removal step can be conducted immediately after this step (b) or at any other time in the process after step (b).

Step (c) involves the protection of the 6-hydroxy substituent if it had not been previously protected. Hydroxy protecting groups are well known in the beta lactam art. A particularly preferred reagent for this step is bis trimethylsilylacetamide which readily forms the trimethylsilyl protecting group at the 6-hydroxy moiety. Preferably step (c) is conducted directly upon the completion of step (b) without isolation of the thiol of formula XVI. Thus the inert solvent utilized, e.g. DMF, may be the same as the one used in step (b). Solvents such as chloroform, methylene chloride and the like may also be employed in step (c). Temperatures for the reaction of step (c) range from 0° C. to 30° C.

Step (d) is wherein the intermediate of formula XVI or XVI(a) is converted to the thiocarbonyl compound of formula XVII by reaction of the compound of formula XVI or XVI(a) with the thiocarbonyl reagent of formula VII. Typically, this step (d) is conducted directly upon the completion of step (c) without isolation of the intermediate of formula XVII or XVI(a). Thus, the solvent utilized may be the same as the one used in step (c). Temperatures for the reaction of step (d) range from about 10° C.–45° C., with room temperature (about 25° C.) being generally preferred. The thiocarbonyl reagent of formula VII has the following structure

$$S=C(-Y)_2 \qquad \text{VII}$$

wherein Y is a leaving group. Typical of such leaving groups are chloro, iodo, imidazolyl or aryloxy such as naphthyloxy. Preferred are 1,1'-thiocarbonyldiimidazole or beta naphthyloxythiocarbonylchloride.

Step (e) involves the cyclization of the compound of formula XVII into the thione of formula IX(a') and IX(b'). The reaction is typically conducted in an anhydrous inert organic solvent such as tetrahydrofuran and the like. An essentially equimolar amount of a strong base such as lithium diisopropyl amide (LDA), lithium di(trimethylsilyl) amine and the like is added to the system to effect cyclization. Typically, the reaction is conducted at from −50° to −100° C., preferably at −70° C., and is generally complete from within 5 minutes to 24 hours.

Step (f) involves the removal of the 6-hydroxy protecting group in the compound of formulas IX(a') and IX(b') to form the compound of formulas IX(a) and IX(b).

Methods for the removal of this group are well known in the beta lactam art. Preferably, when the 6-hydroxy protecting group is trimethylsilyl, addition of a mild aqueous acid solution, such as acetic acid, to the same solution as is employed in step (e) effects removal.

The term "removable hydroxy protecting group" as used herein means any such group conventionally used for this purpose, with the only requirement being compatibility with the hydroxy substituent on the penems and removability utilizing elemental zinc or any other conventional agent for this purpose which will not adversely effect the penem structure. For the purpose of this invention, preferred hydroxy protecting groups include trichloroethyoxycarbonyl, dimethyltributylsilyl, trimethylsilyloxycarbonyl and trimethylsilyl.

Step (g), is wherein the reaction of compounds of formulas IX(a) and IX(b) with compounds of formula XII is conducted in an inert atmosphere, such as nitrogen, in an organic solvent such as tetrahydrofuran (THF). The reaction is completed within 1 to 3 hours to yield allyl-2-(hydrazonoalkylthio)-6-(1-hydroxyethyl)-penem-3-carboxylate compounds of formula XIII.

Removal of the allyl group in Step (h) to yield the compounds of formula I is effected by the addition of the above allyl ester to a solution containing palladium (zero) and an alkali alkylcarboxylate, carboxylic acid or aqueous carbonate. This is described by McCombie in U.S. Pat. No. 4,314,942 which is incorporated herein by reference. Under these conditions, the removal of the allyl group and formation by the alkali salt or the free acid of the compound occurs.

The compounds of formula XII are either known compounds or are prepared from known compounds by conventional processes for preparing hydrazones by reacting the appropriate aldehyde or ketone with a hydrazino compound or an N-amino substituted nitrogen containing heterocyclic compound.

Generally the process is carried out as follows:

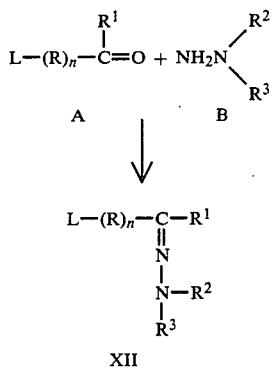

wherein L, n, R, $R^1$, $R^2$ and $R^3$ are as defined hereinabove.

Following the procedures of steps (g) and (h) described hereinabove, compound XII is converted to a compound of formula I.

The following examples illustrate the preparation of the compounds and compositions of this invention.

EXAMPLE 1

PREPARATION OF ALLYL (5R,6S,8R)-2-THIOL-6-(1-HYDROXYETHYL)-PENEM-3-CARBOXYLATE AND ALLYL (5R,6S,8R)-2-THIOCARBONYL-6-(1-HYDROXYETHYL)PENEM-3-CARBOXYLATE (A) Preparation of (3S,4R)-1-(allyloxycarbonylmethyl)-3-(1-hydroxyethyl)-4-(triphenylmethylthio)azetidin-2-one Add 0.3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of alpha-iodo allyl acetate to the system. Stir the system at room temperature for 16 hours. Dilute with ether (50 ml), filter and wash the ether layer with 1% aqueous phosphoric acid, followed by water. After drying over sodium sulfate remove solvent to give a foamy solid.

(B) Preparation of (3S,4R)-3-(1-hydroxyethyl)-1-allyloxycarbonylmethyl-4-sulfhydryl-azetidin-2-one Add 500 mg of (3S,4R)-1-(allyloxycarbonylmethyl)-3-(1-hydroxyethyl)-4-triphenylmethylthio)azetidin-2-one and 20 ml tetrahydrofuran to a 50 ml flask. Add zinc dust and 10% hydrochloric acid in small portions over 1 hour until all of the starting material is reacted. Recover the product by filtering off the excess zinc and removing the solvent to crystallize the title product.

NMR: (CDCl$_3$)=6.2–5.7(1H, m); 5.5–5.15 (2H, m); 5.0 (1H, dd, J=3,9 c/s); 4.75–4.55 (2H,m); 4.45–3.95 (1H,m); 4.14(1H, d, J=18 c/s); 3.78(1H, d, J=18 c/s); 3.19(1H, dd, J=6,3 c/s); 2.09(1H, d, J=9 c/s); 1.34(3H, d, J=6 c/s).

(C) Preparation of (3S,4R)-3-(1-trimethylsilyloxy-ethyl-1-allyloxycarbonylmethyl-4-sulfhydryl-azetidin-2-one Add the entire amount of (3S,4R)-3-(1-hydroxyethyl)-1-allyloxycarbonylmethyl-4-sulfhydryl-azetidin-2-one produced in step (B) above to 25 ml of methylene chloride. To this system add 1.1 ml of bis silylacetamide. Stir the system at room temperature for 15 minutes to give the title compound.

(D) Preparation of (3S,4R)-1-(allyloxycarbonylmethyl)-3-(1-trimethylsilyloxyethyl)-4-(1'-imidazolylthiocarbonylthio)azetidin-2-one After completion of step (C) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

NMR: =8.4, 1H, s; 7.65, 1H, d(J-1 Hz); 7.05, 1H (dJ-1 Hz); 5.95, 1H, d (J=2 Hz); 5.8, 1H,m; 5.45–5.1, 2H, m; 4.3, 1H, m; 4.1, 2H, Q(J-16 Hz); 3.5, d,d (J-2,6); 1.35; 3H, d (J-6 Hz).

(E) Preparation of (5R,6S,8R) allyl-2-thiol-6-(1-trimethylsilyloxyethyl)penem-3-carboxylate and (5R,6S,8R) allyl-2-thiocarbonyl-6-(1-trimethylsilyloxyethyl)penam-3-carboxylate Add 170 mg of (3S,4R)-1-(allyloxycarbonylmethyl)-3-(1-trimethylsilyloxyethyl)-4-(1'-imidazolylthiocarbonylthio)azetidin-2-one to 40 ml of anhydrous tetrahydrofuran under a nitrogen atmosphere. Cool the system to −78° C. and then add 0.6 ml of 1M lithium di(trimethylsilyl) amine in hexane dropwise to the system. Stir the system at −78° C. for 5 minutes. Add 0.2 ml of acetic acid to the system. Dilute the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R) allyl-2-thiol-6-(1-hydroxyethyl)penem-3-carboxylate and (5R,6S,8R) allyl-2-thiocarbonyl-6-(1-hydroxyethyl)penam-3-carboxylate To a 25 ml flask add the entire mixture produced in step (E) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 2

SODIUM (5R,6S,8R)-2-[2-(1,2,4-TRIAZOL-4-YLIMINO)-PROPYLTHIO]-6-(1-HYDROXYETHYL)PENEM-3-CARBOXYLATE

A. Add 3.6 ml Cl—$CH_2COCH_3$ to a mixture of 3.0 g 4-aminotriazole, 150 ml distilled THF and 3.8 ml acetic acid and stir at room temperature for about 7 hours. Add more Cl—$CH_2COCH_3$ (3 ml) and continue stirring overnight, about 15 hours. Concentrate the reaction mixture to a thick colorless oily residue and dissolve in 100 ml $CH_3CN$. Filter through a small silica gel column and elute with $CH_3CN$ to obtain 2-(1,2,4-triazol-4-ylimino)-1-chloropropane as shown by NMR.

B. Add a solution of 1.2 gm chlorohydrazone in 5 ml tetrahydrofuran (THF) and 5 ml water to a mixture of 2 gm of the thione prepared in Example 1, 20 ml THF and 5 ml water. The pH of the reaction mixture was adjusted to about 8.0 with $NaHCO_3$. The reaction was completed in about one-half hour as evidenced by TLC (20% $CH_3CN/CH_2Cl_2$). Remove the THF solvent then add 100 ml $CH_2Cl_2$ and dry over sodium sulfate. Purify by filtering through a silica column and eluting with $CH_3CN$ to obtain the allyl ester of the title compound.

C. Add 0.12 ml 2-ethyl hexanoic acid and 50 mg triphenyl phosphine to a solution of 100 mg of the allyl ester prepared in B above in 5 ml dry $CH_2Cl_2$. Add 20 mg $Pd[P(C_6H_5)_3]_4$ to the resulting solution. The reaction is completed in about one-half hour as confirmed by TLC (20% $CH_3CH$/Ethyl acetate). Add 40 mg sodium hexanoate in ethylacetate to obtain a precipitate of the title compound as a hydroscopic solid.

NMR: $(D_{20})$ δ8.5(s,2H), 5.57 (s,1H), 3.7–4.25 (m,4H), 2.1(s,3H), 1.2(d,3H).

mass spectrum: $FAB[M+H]^+=370$, $[M+Na]^+=392$.

Following the procedures of Example 2 but replacing 4-aminotriazole with imidazol-2-yl hydrazine gives sodium (5R,6S,8R)-2-[2-(imidazol-2-yl hydrazino)propylthio]-6-(1-hydroxyethyl)penem-3-carboxylate.

EXAMPLE 3

SODIUM(5R,6S,8R)-2-[2(N²-CARBAMOYLHYDRAZINO)PROPYLTHIO]-6-(1-HYDROXYETHYL)PENEM-3-CARBOXYLATE

A. Add 1.0 gm chloroacetone and a solution of 0.84 gm $NaHCO_3$ in 10 ml water to a solution of 1.1 gm semicarbazide hydrochloride in 25 ml THF and stir overnight. Two layers form. Separate the top layer and concentrate to obtain an off-white solid, 2-semicarbazono-1-chloropropane.

B. Add 1.2 gm of the semicarbazone prepared in A above in 5 ml water to a mixture of 2.0 gm of the thione prepared in Example 1, 30 ml THF, 10 ml water and 0.6 gm $NaHCO_3$. Stir the mixture for about one-half hour to complete the reaction as evidenced by TLC (20% $CH_3CN$/ethylacetate). Remove the THF solvent to obtain a solid. Work up the solid and recover the allyl ester of the title compound.

C. Add 10 mg $Pd[P(C_6H_5)_3]_4$ to a solution of 100 mg of the allyl ester prepared in B above, 50 mg triphenyl phosphine and 0.2 ml 2-ethylhexanoic acid in 10 ml THF. After one-half hour add 40 mg Na-ethylhexanoate to cause a precipitate to gradually form. When the precipitation stops the reaction is completed. Remove the THF solvent at room temperature and add 10 ml ethylacetate. Filter off the solid and work up then lyophilize to obtain the title compound as a white solid.

NMR $(D_{20})$: δ5.3(d,1H), 3.9(m,1H), 3.55(d of d, 1H), 1.7(s,3H), 1.0(d,3H

Mass spectrum: FAB. $[M+H]^+=361$, $[M+Na]^+=383$.

Following the procedures of examples 2 and 3 but replacing the starting compounds with appropriately substituted analogous reagents A and B which are known or can be prepared by methods known in the art for preparing analogous compounds, the compounds of formula I are prepared. The following table shows the hydrazone moiety which results when reagent A is

and reagent B is as in the table.

TABLE

| Reagent B | Hydrazone |
|---|---|
| $H_2N-N\langle\text{triazole}\rangle$ (with =N) | $=N-N\langle\text{triazole}\rangle$ |
| $H_2N-NH-CH_2CH_2OH$ | $=N-NHCH_2CH_2OH$ |
| $H_2N-N\langle\text{morpholine, O}\rangle$ | $=N-N\langle\text{morpholine, O}\rangle$ |
| $H_2N-N\langle\text{thiomorpholine, S}\rangle$ | $=N-N\langle\text{thiomorpholine, S}\rangle$ |
| $H_2N-N\langle\text{ring, }SO_2\rangle$ | $=N-N\langle\text{ring, }SO_2\rangle$ |
| $H_2N-N\langle\text{piperazine, }N-R_1\rangle$ | $=N-N\langle\text{piperazine, }NR_1\rangle$ |
| $H_2N-NH-C(=O)-N\langle\text{ring with 2 C=O, }N-R_1\rangle$ | $=N-NH-C(=O)-N\langle\text{ring with 2 C=O, }N-R_1\rangle$ |
| $H_2N-NH-C(=O)-N\langle\text{ring with 2 C=O, }NH, R_1\rangle$ | $=N-NH-C(=O)-N\langle\text{ring with 2 C=O, }NH, R_1\rangle$ |
| $H_2N-NH-\langle\text{imidazole with }R_1\rangle$ | $=N-NH-\langle\text{imidazole with }R_1\rangle$ |

$R_1$ is lower alkyl, $-CONH_2$, $-SO_2NH_2$ OR H

TABLE-continued

| Reagent B | Hydrazone |
|---|---|
| H$_2$N—NH—[thiazole ring with S, N] | =N—NH—[thiazole ring with S, N] |
| H$_2$N—NH—[oxazole ring with O, N] | =N—NH—[oxazole ring with O, N] |
| H$_2$N—NH—[cyclopropyl] | =N—NH—[cyclopropyl] |
| H$_2$N—NH—CH$_3$ | =N—NH—CH$_3$ |
| H$_2$N—NH—CH$_2$CH$_3$ | =N—NH—CH$_2$CH$_3$ |
| H$_2$N—NH—CH(CH$_3$)$_2$ | =N—NH—CH(CH$_3$)$_2$ |

In the following examples, the Active Ingredient is sodium(5R,6S,8R)-2-[2-(1,2,4-triazol-4-ylimio)propyl-thio]-6-(1-hydroxyethyl)penem-3-carboxylate; sodium(5R,6S,8R)-2-[2(N$^2$-carbamoylhydrazino)-propylthio]-6-(1-hydroxyethyl)penem-3-carboxylate; or equivalent amount of a penem of a compound of formula I.

EXAMPLE 4

Capsules

| No. | Ingredient | mg/tablet | mg/tablet |
|---|---|---|---|
| 1. | Active Ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
|  | Total | 500 | 650 |

Method of Manufacture

Mix Items Nos. 1, 2, 3 and 4 in a suitable mixer for 10-15 minutes. Add Item No. 5 and mix for 1-3 minutes. Fill the mixture into suitable two-piece hard gelatin capsules using encapsulating machine.

EXAMPLE 5

Tablets

| No. | Ingredient | mg/tablet | mg/tablet |
|---|---|---|---|
| 1. | Active Ingredient | 250 | 500 |
| 2. | Lactose USP | 57 | 114 |
| 3. | Corn Starch, Food Grade 10% paste in Purified Water | 20 | 40 |
| 4. | Corn Starch, Food Grade | 18 | 39 |
| 5. | Magnesium Stearate NF | 5 | 7 |
|  | Total | 350 | 700 |

Method of Manufacture

Mix Item Nos. 1 and 2 in a suitable mixer for 10-15 minutes. Granulate the mixture with Item No. 3. Past the wet granulation through a coarse screen (e.g., ¼") if needed, and dry the wet granules. Mill the dried granules. Combine Item No. 4 and dried granules and mix for 10-15 minutes. Add Item No. 5 and mix for 1-3 minutes. Compress the mixture to appropriate size and weight on a suitabe tablet machine.

EXAMPLE 6

| Injectable Powder: (per vial) | | |
|---|---|---|
|  | g/vial | g/vial |
| Active Ingredient | 0.5 | 1.0 |

Add sterile water for injection or bacteriostatic water for injection for reconstitution.

EXAMPLE 7

| Injectable Solution | | |
|---|---|---|
| Ingredient | mg/ml | mg/ml |
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 1.5 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°-70° C.
2. Cool to 25°-35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 micron membrane and fill into appropriate containers.
6. Terminally sterilize the units by autoclaving.

EXAMPLE 8

| Injectable Powder: (per vial) | |
|---|---|
|  | g/vial |
| Active Ingredient | 1.0 |
| Sodium Citrate | 0.05 | pH is adjusted to 6.2 using 0.1 N citric acid solution.

Add sterile water for injection or bacteriostatic water for injection for reconstitution.

We claim:

1. Compounds represented by the formula $$\begin{array}{c}\text{H}-\text{C}\diagup^{\text{OH}}\\ \text{CH}_3\diagup\end{array}\diagdown\begin{array}{c}\text{S}\\ \text{N}\end{array}\diagdown\begin{array}{c}\text{S}-(\text{R})_n-\overset{\text{O}}{\underset{\|}{\text{C}}}-\text{R}^1\\ \text{COOH}\quad\text{N}\diagup^{\text{N}}\diagdown_{\text{R}^2}\\ \text{R}^3\end{array}$$

and pharmaceutically acceptable salts and pharmaceutically acceptable esters thereof, in racemic or optically active forms, wherein n is one or two;

R represents

wherein R⁴ and R⁵ are independently selected from hydrogen, lower alkyl, hydroxy-lower alkyl, halo-lower alkyl, amino-lower alkyl, carbamido-lower alkyl, cyano-lower alkyl, carbamoyloxy-lower alkyl, carbamoyl-lower alkyl, carboxy-lower alkyl, heterocyclyl-lower alkyl wherein the heterocyclic moiety has 5 or 6 ring atoms, at least one of which is carbon, and the remaining 4 or 5 ring atoms are independently selected from carbon, nitrogen, oxygen and sulfur; or R⁴ and R⁵ taken together are =O;

R¹ represents hydrogen, lower alkyl, hydroxy-lower alkyl, amino-lower alkyl, carboxy-lower alkyl, carbamoyloxy-lower alkyl, carbamoyl-lower alkyl, haloloweralkyl, cyano-lower alkyl, heterocyclic or heterocyclyl-lower alkyl wherein the heterocyclic moiety has 5 or 6 ring atoms, at least one of which is carbon, and the remaining ring atoms are independently selected from oxygen, carbon nitrogen and sulfur;

R² and R³ independently represent hydrogen, carbamoyl, lower alkyl, carboxy-loweralkyl, hydroxy-lower alkyl, amino-lower alkyl, imidazolyl-lower alkyl, triazolyl-lower alkyl, tetrazolyl-lower alkyl, pyridinium-lower alkyl, aryl or R² and R³ together with the N to which they are attached are a heterocyclic of 5 or 6 ring atoms, at least one of which is carbon and the remaining ring atoms are independently selected from carbon and nitrogen, wherein said heterocyclic moiety is unsubstituted or substituted with lower alkyl, hydroxy-lower alkyl, amino-lower alkyl, carboxy-lower alkyl, carboxyl, amino, hydroxy, imidazole-lower alkyl, triazole-lower alkyl, tetrazole-lower alkyl or pyridinium-lower alkyl.

2. Compounds of claim 1 wherein R¹ is hydrogen or lower alkyl, one of R² and R³ are each independently hydrogen or carbamoyl or taken together with the nitrogen to which they are attached R² and R³ are a heterocyclic ring of 5 or 6 ring atoms at least one of which is carbon and the remaining ring atoms are independently selected from nitrogen and carbon and R⁴ and R⁵ are each hydrogen.

3. A compound of claim 1 which is (5R,6S,8R)-2-[2-(1,2,4-triazol-4-ylimino)-propylthio]-6-(1-hydroxyethyl)penem-3-carboxylic acid.

4. A compound of claim 1 which is (5R,6S,8R)-2-[2(N²-carbamoylhydrazino)-propylthio]-6-(1-hydroxyethyl)penem-3-carboxylic acid.

5. A pharmaceutical composition comprising an antibacterial effective amount of a compound of claim 1 in admixture with a pharmaceutically acceptable carrier therefor.

6. A composition according to claim 5 wherein said antibacterial compound is (5R,6S,8R)-2-[2-(1,2,4-triazol-4-ylimino)-propylthio]-6-(1-hydroxyethyl)-penem-3-carboxylic acid.

7. A composition according to claim 5 wherein said antibacterial compound is (5R,6S,8R)-2-[2(N²-carbamoylhydrazino)-propylthio]-6-(1-hydroxyethyl)-penem-3-carboxylic acid.

8. A method of preventing bacterial infections in patients in need of such treatment which comprises administering an antibacterial effective amount of a compound of claim 1.

9. The method of claim 8 wherein the compound administered is 5R,6S,8R)-2-[2-(1,2,4-triazol-4-ylimino)-propylthio]-6-(1-hydroxyethyl)penem-3-carboxylic acid.

10. The method of claim 9 wherein the compound administered is (5R,6S,8R)-2-[2(N²-carbamoylhydrazino)propylthio]-6-(1-hydroxyethyl)penem-3-carboxylic acid.

* * * * *